United States Patent
D'Ambrogio et al.

(10) Patent No.: US 6,184,190 B1
(45) Date of Patent: Feb. 6, 2001

(54) AQUEOUS SOLUTION OF AN ALPHA SULFONATE SURFACTANT COMPRISING 1,3-BIS (HYDROXYMETHYL)-5, 5-DIMETHYLIMIDAZOLIDINE-2, 4 DIONE

(75) Inventors: Robert D'Ambrogio, Bound Brook; Kurt Sackariasen, Sea Girt; Robert Heffner, Somerset, all of NJ (US)

(73) Assignee: Colgate-Palmolive Co., Piscataway, NJ (US)

( * ) Notice: Under 35 U.S.C. 154(b), the term of this patent shall be extended for 0 days.

(21) Appl. No.: 09/590,064

(22) Filed: Jun. 8, 2000

(51) Int. Cl.[7] ........................................ A61K 7/50
(52) U.S. Cl. .................. 510/130; 510/119; 510/123; 510/121; 510/125
(58) Field of Search ..................................... 510/121, 119, 510/130, 123, 125

(56) References Cited

U.S. PATENT DOCUMENTS

| | | | |
|---|---|---|---|
| 6,030,931 | * | 2/2000 | Vinski et al. ........................ 510/130 |
| 6,066,613 | * | 5/2000 | Tsaur et al. .......................... 510/403 |
| 6,077,816 | * | 6/2000 | Puvvada et al. ..................... 510/130 |
| 6,080,708 | * | 6/2000 | Glenn, Jr. et al. ................... 510/130 |

* cited by examiner

Primary Examiner—Necholus Ogden
(74) Attorney, Agent, or Firm—Richard E. Nanfeldt

(57) ABSTRACT

The present invention relates to a process for preparing an aqueous solution of a $C_{14}$–$C_{16}$ alpha olefin sulfonate, wherein the aqueous solution has a Klett color of less than 12, when diluted with water to a 5% solution.

5 Claims, No Drawings

AQUEOUS SOLUTION OF AN ALPHA SULFONATE SURFACTANT COMPRISING 1,3-BIS (HYDROXYMETHYL)-5, 5-DIMETHYLIMIDAZOLIDINE-2, 4 DIONE

FIELD OF THE INVENTION

The present invention relates to a method of producing a colorless aqueous solution of an alpha olefin sulfonate which can be subsequently used in the formation of cleaning compositions.

BACKGROUND OF THE INVENTION

Alpha olefin sulfonates are used in liquid dish cleaning compositions and hard surface cleaning compositions.

Commercial alpha olefin sulfonate surfactants are usually supplied as a 35 to 45 wt. % aqueous solution. These solutions have a distinctive yellowish color which limits the use of alpha olefin sulfonate surfactant in colorless liquid cleaning compositions. The present inventions teach a method of producing a colorless aqueous solution of 35 wt. % to 45 wt. % of alpha olefin sulfonate from a commercial 35 wt. % to 45 wt. % aqueous solution of alpha olefin sulfonate which is yellowish in color. The addition of hydrogen peroxide and caustic soda to the commercially aqueous solution of the alpha olefin sulfonate causes oxidation of the containments which cause the yellowish color.

SUMMARY OF THE INVENTION

The instant invention relates to a process for producing an aqueous solution of about 5 wt. % of a $C_{14}$–$C_{16}$ alpha olefin sulfonate which has a Klett color of less than about 12, preferably less than about 11 and most preferably less than about 10.

The present invention also relates to 30 to 40 wt. % solution of a $C_{14}$–$C_{16}$ alpha olefin sulfonate. When the 30 to 40 wt. % solution of the $C_{14}$–$C_{16}$ alpha olefin sulfonate is diluted with water to a 5 wt. % aqueous solution of the $C_{14}$–$C_{16}$ alpha olefin sulfonate, the 5 wt. % solution of the $C_{14}$–$C_{16}$ alpha olefin sulfonate has a Klett color of less than about 12, more preferably less than about 11 and most preferably less than about 10.

The present invention further relates to cleaning compositions having improved color.

DETAILED DESCRIPTION OF THE INVENTION

The present invention relates to a process for forming a solution of 30 wt. % to 40 wt. % of a $C_{14}$–$C_{16}$ alpha olefin sulfonate and 60 wt. % to 70 wt. % of water, wherein the solution, when diluted to 5 wt. %, with distilled water has a Klett color of less than 12, preferably less than 11 and most preferably less than 10 which comprises the steps of:

(a) forming a solution having a pH of 10 to 12 by adding of 0.001 wt. % to 0.1 wt. % of sodium hydroxide to 99.9 wt. % to 99.999 wt. % of an initial solution of 30 wt. % to 40 wt. % of a $C_{14}$–$C_{16}$ alpha olefin sulfonate and 40 wt. % to 60 wt. % of water having a pH of 7.5 to 9.5, wherein said initial solution when diluted to 5 wt. % of $C_{14}$–$C_{16}$ alpha olefin sulfonate has a Klett color of greater than 20;

(b) adding 1 wt. % to 2 wt. % of a 25 wt. % to 35 wt. % hydrogen peroxide solution to said 30 wt. % to 40 wt. % solution of alpha olefin sulfonate;

(c) mixing for 6 hours to 48 hours at 77° F. to 150° F. the 30 wt. % to 40 wt. % solution of $C_{14}$–$C_{16}$ alpha olefin sulfonate, sodium hydroxide and hydrogen peroxide, wherein said solution has a pH of about 7 to about 9;

(d) adding 0.001 wt. % to 0.005 wt. % of an alkali metal hydroxide such as sodium hydroxide to said 30 wt. % to 40 wt. % solution of $C_{14}$–$C_{16}$ alpha olefin solution, sodium hydroxide and hydrogen peroxide to form said color improved solution of said $C_{14}$–$C_{16}$ alpha olefin sulfonate having a pH of about 10 to about 12 which when diluted to 5 wt. % of said $C_{14}$–$C_{16}$ alpha olefin sulfonate has a Klett color of less than 12, preferably less than 11, and most preferably less than 10.

The present invention also relates to a solution of 30 wt. % to 40 wt. % of a $C_{14}$–$C_{16}$ alpha olefin sulfonate and 60 wt. % to 70 wt. % of water which said solution has a pH of about 10 to about 12 and when diluted to 5 wt. % of said $C_{14}$–$C_{16}$ alpha olefin sulfonate has a Klett color of less than 12, preferably less than 11 and most preferably less than 10.

An object of the present invention is to provide a cleaning composition having improved color wherein said cleaning composition contains an aqueous solution of a $C_{14}$–$C_{16}$ alpha olefin sulfonate, wherein a 5 wt. % aqueous solution of said $C_{14}$–$C_{16}$ alpha olefin sulfonate has a Klett color of less than 12, preferably less than 11 and most preferably less than 10.

The present invention also relates to light duty liquid cleaning composition comprising approximately by weight:

(a) 3% to 50% of a 30% to 40% aqueous solution of a $C_{14}$–$C_{16}$ alpha olefin sulfonate, wherein the 30% to 40% aqueous solution of said $C_{14}$–$C_{16}$ alpha olefin sulfonate which has a Klett color of less than 12 when diluted with water to a 5% aqueous solution of said $C_{14}$–$Cl_6$ alpha olefin sulfonate;

(b) 0.5% to 35% of at least one surfactant selected from the group consisting of ethoxylated nonionic surfactants, ethoxylated/propoxylated nonionic surfactant, zwitterionic surfactants, amine oxide surfactants, alkyl monoalkanol amide, paraffin sulfonate surfactants, linear alkyl benzene sulfonate surfactants, alkyl sulfate surfactants, ethoxylated alkyl ether sulfate surfactants, $C_{12}$–$C_{14}$ fatty acid alkanol amides, and alkyl polyglucoside surfactants and mixtures thereof;

(c) 0 to 15%, more preferably 0.1% to 8% of at least one solubilizing agent;

(d) 0 to 2.5%, more preferably 0.1% to 1.5% of a proton donating agent;

(e) 0 to 3%, more preferably 0.1% to 2% of a disinfecting agent; and (f) the balance being water.

The present invention also relates to a body cleaning composition:

(a) 3% to 30% of a 30% to 40% of said $C_{14}$–$C_{16}$ alpha olefin sulfonate which aqueous solution of a $C_{14}$–$C_{16}$ alpha olefin sulfonate, wherein 30% to 40% of the aqueous solution has a Klett color of less than 12 when diluted with water to a 5% aqueous solution of said $C_{14}$–$C_{16}$ alpha olefin sulfonate;

(b) 0.1% to 8% of a $C_8$–$C_{16}$ alkyl polyglucoside preferably decyl polyglucoside;

(c) 0.05% to 2%, more preferably 0.1% to 1% of a disinfecting agent;

(d) 0.1% to 8%, more preferably 0.5% to 6% of a zwitterionic surfactant;

(e) 0 to 1.5%, more preferably 0.1% to 1% of a proton donating agent;

(f) 0.05% to 2.5% of an alkali metal halide such as sodium chloride;

(g) 0.05% to 1%, more preferably 0.1% to 0.8% of 1,3-Bis(Hydroxy methyl)-5,5-Dimethylimidazolidine-2,4-dione(+) which is manufactured by Lonza, Inc. under the tradename of Glydant Plum™; and (h) the balance being water, wherein the composition has a pH of about 2.8 to about 7.0 and a Brookfield viscosity at 25° C., 20 rpms, #4 spindle of about 2,500 to about 6,500 cps.

The water soluble nonionic surfactants utilized in this invention are commercially well known and include the primary aliphatic alcohol ethoxylates, secondary aliphatic alcohol ethoxylates, alkylphenol ethoxylates and ethylene-oxide-propylene oxide condensates on primary alkanols, such a Plurafacs (BASF) and condensates of ethylene oxide with sorbitan fatty acid esters such as the Tweens (ICI). The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethylene oxide chain can be adjusted to achieve the desired balance between the hydrophobic and hydrophilic elements.

The nonionic detergent class includes the condensation products of a higher alcohol (e.g., an alkanol containing 8 to 18 carbon atoms in a straight or branched chain configuration) condensed with 5 to 30 moles of ethylene oxide, for example, lauryl or myristyl alcohol condensed with 16 moles of ethylene oxide (EO), tridecanol condensed with 6 to moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to 14 carbon atoms in length and wherein the condensate contains either 6 moles of EO per mole of total alcohol or 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohols containing about 9–15 carbon atoms, such as $C_9$–$Cl_{11}$ alkanol condensed with 8 moles of ethylene oxide (Neodol 91-8), $C_{12-13}$ alkanol condensed with 6.5 moles ethylene oxide (Neodol 23-6.5), $C_{12-15}$ alkanol condensed with 12 moles ethylene oxide (Neodol 25-12), $C_{14-15}$ alkanol condensed with 13 moles ethylene oxide (Neodol 45-13), and the like. Such ethoxamers have an HLB (hydrophobic lipophilic balance) value of 8–15 and give good emulsification, whereas ethoxamers with HLB values below 8 contain less than 5 ethyleneoxy groups and tend to be poor emulsifiers and poor detergents.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$–$C_{15}$ secondary alkanol condensed with either 9 EO (Tergitol 15-S-9) or 12 EO (Tergitol 15-S-12) marketed by Union Carbide.

Other suitable nonionic detergents include the polyethylene oxide condensates of one mole of alkyl phenol containing from 8 to 18 carbon atoms in a straight— or branched chain alkyl group with 5 to 30 moles of ethylene oxide. Specific examples of alkyl phenol ethoxylates include nonyl condensed with 9.5 moles of EO per mole of nonyl phenol, dinonyl phenol condensed with 12 moles of EO per mole of phenol, dinonyl phenol condensed with 15 moles of EO per mole of phenol and di- isooctylphenol condensed with 15 moles of EO per mole of phenol. Commerically available nonionic surfactants of this type include Igepal CO-630 (nonyl phenol ethoxylate) marketed by GAF Corporation.

Also among the satisfactory nonionic detergents are the water-soluble condensation products of a $C_8$–$C_{20}$ alkanol with a etheric mixture of ethylene oxide and propylene oxide wherein the weight ratio of ethylene oxide to propylene oxide is from 2.5:1 to 4:1, preferably 2.8:1–3.3:1, with the total of the ethylene oxide and propylene oxide (including the terminal ethanol or propanol group) being from 60–85%, preferably 70–80%, by weight. Such detergents are commercially available from BASF-Wyandotte and a particularly preferred detergent is a $C_{10}$–$C_{16}$ alkanol condensate with ethylene oxide and propylene oxide, the weight ratio of ethylene oxide to propylene oxide being 3:1 and the total alkoxy content being 75% by weight.

Other suitable water-soluble nonionic detergents which are less preferred are marketed under the trade name "Pluronics." The compounds are formed by condensing ethylene oxide with a hydrophobic base formed by the condensation of propylene oxide with propylene glycol. The molecular weight of the hydrophobic portion of the molecule is of the order of 950 to 4,000 and preferably 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants will be in liquid form and satisfactory surfactants are available as grades L62 and L64.

Suitable water-soluble non-soap, anionic surfactants used in the instant compositions include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble detergent. Usually, the hydrophobic group will include or comprise a $C_8$–$C_{22}$ alkyl, alkyl or acyl group. Such surfactants are employed in the form of water-soluble salts and the salt-forming cation usually is selected from the group consisting of sodium, potassium, ammonium, magnesium and mono-, di- or tri-$C_2$–$C_3$ alkanolammonium, with the sodium, magnesium and ammonium cations again being preferred.

Examples of suitable sulfonated anionic surfactants are the well known higher alkyl mononuclear aromatic sulfonates such as the higher alkyl benzene sulfonates containing from 10 to 16 carbon atoms in the higher alkyl group in a straight or branched chain, $C_8$–$C_{15}$ alkyl toluene sulfonates and $C_8$–$C_{15}$ alkyl phenol sulfonates.

A preferred sulfonate is linear alkyl benzene sulfonate having a high content of 3- (or higher) phenyl isomers and a correspondingly low content (well below 50%) of 2- (or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low. Particularly preferred materials are set forth in U.S. Pat. No. 3,320,174.

Other examples of suitable anionic sulfonate surfactants are the paraffin sulfonates containing 10 to 20, preferably 13 to 17, carbon atoms. Primary paraffin sulfonates are made by reacting long-chain alpha olefins and bisulfites and paraffin sulfonates having the sulfonate group distributed along the paraffin chain are shown in U.S. Pat. Nos. 2,503,280; 2,507,088; 3,260,744; 3,372,188; and German Patent 735, 096.

Examples of satisfactory anionic sulfate surfactants are the $C_8$–$C_{18}$ alkyl sulfate salts and the $C_8$–$C_{18}$ alkyl sulfate salts and the $C_8$–$C_{18}$ alkyl ether polyethenoxy sulfate salts having the formula $R(OC_2H_4)_n OSO_3M$ wherein n is 1 to 12, preferably 1 to 5, and M is a metal cation selected from the group consisting of sodium, potassium, ammonium, magnesium and mono-, di- and triethanol ammonium ions. The alkyl sulfates may be obtained by sulfating the alcohols obtained by reducing glycerides of coconut oil or tallow or mixtures thereof and neutralizing the resultant product.

On the other hand, the alkyl ether polyethenoxy sulfates are obtained by sulfating the condensation product of ethylene oxide with a $C_8$–$C_{18}$ alkanol and neutralizing the resultant product. The alkyl sulfates may be obtained by sulfating the alcohols obtained by reducing glycerides of coconut oil or tallow or mixtures thereof and neutralizing the resultant product. On the other hand, the alkyl ether polyethenoxy sulfates are obtained by sulfating the condensation product of ethylene oxide with a $C_8$–$C_{18}$ alkanol and neutralizing the resultant product. The alkyl ether polyethenoxy sulfates differ from one another in the number of moles of ethylene oxide reacted with one mole of alkanol. Preferred alkyl sulfates and preferred alkyl ether polyethenoxy sulfates contain 10 to 16 carbon atoms in the alkyl group.

The $C_8$–$C_{12}$ alkylphenyl ether polyethenoxy sulfates containing from 2 to 6 moles of ethylene oxide in the molecule also are suitable for use in the inventive compositions. These surfactants can be prepared by reacting an alkyl phenol with 2 to 6 moles of ethylene oxide and sulfating and neutralizing the resultant ethoxylated alkylphenol.

Other suitable anionic surfactants are the $C_9$–$C_{15}$ alkyl ether polyethoxyl carboxylates having the structural formula $R(OC_2H_4)_nOX$ COOH wherein n is a number from 4 to 12, preferably 5 to 10 and X is selected from the group consisting of

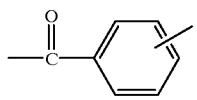

wherein $R_1$ is a $C_1$–$C_3$ alkylene group. Preferred compounds include $C_9$–$C_{11}$ alkyl ether polyethenoxy (7-9) C(O) CH$_2$CH$_2$COOH, $C_{13}$–$C_{15}$ alkyl ether polyethenoxy (7-9)

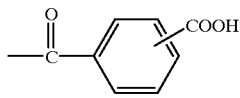

and $C_{10}$–$C_{12}$ alkyl ether polyethenoxy (5-7) CH2COOH. These compounds may be prepared by considering ethylene oxide with appropriate alkanol and reacting this reaction product with chloracetic acid to make the ether carboxylic acids as shown in U.S. Pat. No. 3,741,911 or with succinic anhydride or phthalic anhydride. Obviously, these anionic surfactants will be present either in acid form or salt form depending upon the pH of the final composition, with salt forming cation being the same as for the other anionic surfactants.

The water-soluble zwitterionic surfactant provides good foaming properties and mildness to the present compositions. The zwitterionic surfactant is a water soluble betaine having the general formula:

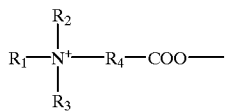

wherein $R_1$ is an alkyl group having 10 to 20 carbon atoms, preferably 12 to 16 carbon atoms, or the amido radical:

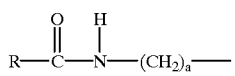

wherein R is an alkyl group having 9 to 19 carbon atoms and a is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N, N-dimethyl-ammonia)acetate, coco dimethyl betaine or 2-coco, N,N-dimethylammonio)acetate, myristyl dimethyl betaine, palmityl dimethyl betaine, lauryl diemethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine.

Another useful zwitterionic surfactant is a sultaine which is depicted by the formula:

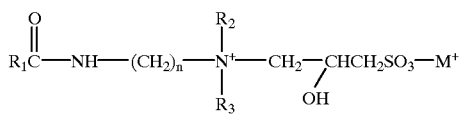

wherein $R_1$ is a saturated or unsaturated alkyl group having about 6 to about 24 carbon atoms, $R_2$ is a methyl or ethyl group, $R_3$ is a methyl or ethyl group, n is about 1 to about 6, and $M^+$ is an alkali metal cation. The most preferred hydroxysultaine is a potassium salt of cocoamidopropyl hydroxysultaine.

Amine oxide semi-polar nonionic surfactants comprise compounds and mixtures of compounds having the formula

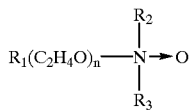

wherein $R_1$ is an alkyl, 2-hydroxyalkyl, 3-hydroxyalkyl, or 3-alkoxy-2-hydroxypropyl radical in which the alkyl and alkoxy, respectively, contain from 8 to 18 carbon atoms, $R_2$ and $R_3$ are each methyl, ethyl, propyl, isopropyl, 2-hydroxyethyl, 2-hydroxypropyl, or 3-hydroxypropyl, and n is from 0 to 10. Particularly preferred are amine oxides of the formula:

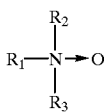

wherein $R_1$ is a $C_{12-16}$ alkyl and $R_2$ and $R_3$ are methyl or ethyl. The above ethylene oxide condensates, amides, and amine oxides are more fully described in U.S. Pat. No. 4,316,824 which is hereby incorporated herein by reference.

The alkyl polysaccharides surfactants, which are used in conjunction with the aforementioned surfactant have a hydrophobic group containing from about 8 to about 20 carbon atoms, preferably from about 10 to about 16 carbon atoms, most preferably from about 12 to about 14 carbon atoms, and polysaccharide hydrophilic group containing from about 1.5 to about 10, preferably from about 1.5 to about 4, most preferably from about 1.6 to about 2.7 saccharide units (e.g., galactoside, glucoside, fructoside, glucosyl, fructosyl; and/or galactosyl units). Mixtures of saccharide moieties may be used in the alkyl polysaccharide surfactants. The number x indicates the number of saccharide units in a particular alkyl polysaccharide surfactant. For a particular alkyl polysaccharide molecule x can only assume integral values. In any physical sample of alkyl polysaccharide surfactants there will be in general molecules having different x values. The physical sample can be characterized by the average value of x and this average value can assume non-integral values. In this specification the values of x are to be understood to be average values. The hydrophobic group (R) can be attached at the 2-, 3-, or 4-positions rather than at the 1-position, (thus giving e.g. a glucosyl or galactosyl as opposed to a glucoside or galactoside). However, attachment through the 1-position, i.e., glucosides, galactoside, fructosides, etc., is preferred. In the preferred product the additional saccharide units are predominately attached to the previous saccharide unit's 2-position. Attachment through the 3-, 4-, and 6-positions can also occur. Optionally and less desirably there can be a polyalkoxide chain joining the hydrophobic moiety (R) and the polysaccharide chain. The preferred alkoxide moiety is ethoxide.

Typical hydrophobic groups include alkyl groups, either saturated or unsaturated, branched or unbranched containing from about 8 to about 20, preferably from about 10 to about 18 carbon atoms. Preferably, the alkyl group is a straight chain saturated alkyl group. The alkyl group can contain up to 3 hydroxy groups and/or the polyalkoxide chain can contain up to about 30, preferably less than about 10, alkoxide moieties.

Suitable alkyl polysaccharides are decyl, dodecyl, tetradecyl, pentadecyl, hexadecyl, and octadecyl, di-, tri-, tetra-, penta-, and hexaglucosides, galactosides, lactosides, fructosides, fructosyls, lactosyls, glucosyls and/or galactosyls and mixtures thereof.

The alkyl monosaccharides are relatively less soluble in water than the higher alkyl polysaccharides. When used in admixture with alkyl polysaccharides, the alkyl monosaccharides are solubilized to some extent. The use of alkyl monosaccharides in admixture with alkyl polysaccharides is a preferred mode of carrying out the invention. Suitable mixtures include coconut alkyl, di-, tri-, tetra-, and pentaglucosides and tallow alkyl tetra-, penta-, and hexaglucosides.

The preferred alkyl polysaccharides are alkyl polyglucosides having the formula

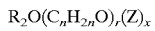

wherein Z is derived from glucose, R is a hydrophobic group selected from the group consisting of alkyl, alkylphenyl, hydroxyalkylphenyl, and mixtures thereof in which said alkyl groups contain from about 10 to about 18, preferably from about 12 to about 14 carbon atoms; n is 2 or 3 preferably 2, r is from 0 to 10, preferable 0; and x is from 1.5 to 8, preferably from 1.5 to 4, most preferably from 1.6 to 2.7. To prepare these compounds a long chain alcohol ($R_2OH$) can be reacted with glucose, in the presence of an acid catalyst to form the desired glucoside. Alternatively the alkyl polyglucosides can be prepared by a two step procedure in which a short chain alcohol ($R_1OH$) can be reacted with glucose, in the presence of an acid catalyst to form the desired glucoside. Alternatively the alkyl polyglucosides can be prepared by a two step procedure in which a short chain alcohol ($C_{1-6}$) is reacted with glucose or a polyglucoside (x=2 to 4) to yield a short chain alkyl glucoside (x=1 to 4) which can in turn be reacted with a longer chain alcohol ($R_2OH$) to displace the short chain alcohol and obtain the desired alkyl polyglucoside. If this two step procedure is used, the short chain alkylglucosde content of the final alkyl polyglucoside material should be less than 50%, preferably less than 10%, more preferably less than about 5%, most preferably 0% of the alkyl polyglucoside.

The amount of unreacted alcohol (the free fatty alcohol content) in the desired alkyl polysaccharide surfactant is preferably less than about 2%, more preferably less than about 0.5% by weight of the total of the alkyl polysaccharide. For some uses it is desirable to have the alkyl monosaccharide content less than about 10%.

The used herein, "alkyl polysaccharide surfactant" is intended to represent both the preferred glucose and galactose derived surfactants and the less preferred alkyl polysaccharide surfactants. Throughout this specification, "alkyl polyglucoside" is used to include alkyl polyglycosides because the stereochemistry of the saccharide moiety is changed during the preparation reaction.

An especially preferred APG glycoside surfactant is APG 625 glycoside manufactured by the Henkel Corporation of Ambler, Pa. APG25 is a nonionic alkyl polyglycoside characterized by the formula:

wherein n=10 (2%); n=122 (65%); n=14 (21–28%); n=16 (4–8%) and n=18 (0.5%) and x (degree of polymerization)= 1.6. APG 625 has: a pH of 6 to 10 (10% of APG 625 in distilled water); a specific gravity at 25° C. of 1.1 g/ml; a density at 25° C of 9.1 lbs/gallon; a calculated HLB of 12.1 and a Brookfield viscosity at 35° C., 21 spindle, 5–10 RPM of 3,000 to 7,000 cps.

The instant light duty liquid cleaning composition can contain at least one solubilizing agent selected from the group consisting of alkali metal chlorides such as sodium chloride, $C_1$–$C_4$ alkanols such as ethanol, alkali metal salts of cumene sulfonate or xylene sulfonate and urea and mixtures thereof.

The surfactants together with the aqueous solution of the $C_{14}$–$C_{16}$ alpha olefin sulfonate are solubilized in the water. To the composition can also be added water soluble hydrotropic salts include sodium, potassium, ammonium and mono-, di- and triethanolammonium salts. While the aqueous medium is primarily water, preferably said solubilizing agents are included in order to control the viscosity of the liquid composition and to control low temperature cloud clear properties. Usually, it is desirable to maintain clarity to a temperature in the range of 5° C. to 10° C. Therefore, the proportion of solubilizer generally will be from 1%–15%, preferably 2%–12%, most preferably 2%–8%, by weight of the detergent composition with the proportion of ethanol, when present, being 5% of weight or less in order to provide a composition having a flash point above 46° C. Preferably the solubilizing ingredient will be a mixture of ethanol and either sodium xylene sulfonate or sodium cumene sulfonate or a mixture of said sulfonates or ethanol and urea. Inorganic salts such as sodium sulfate, magnesium sulfate, sodium chloride and sodium citrate can be added at concentrations of 0.5 to 4.0 wt. % to modify the cloud point of the nonionic surfactant and thereby control the haze of the resultant solution. Various other ingredients such as urea at a concentration of 0.5 to 4.0 wt. % or urea at the same concentration in combination with ethanol at a concentration of 0.5 to 4.0 wt. % can be used as solubilizing agents. Other ingredients which have been added to the compositions at concentrations of 0.1 to 4.0 wt. percent are perfumes, sodium bisulfite, ETDA, isoethanoeic acid and proteins such as lexine protein. The foregoing solubilizing ingredients also facilitate the manufacture of the inventive compositions because they tend to inhibit gel formation.

The disinfecting agent is selected from the group consisting of quaternary ammonium compound triclosan, perfumes, essential oils and mixtures thereof.

As used herein and in the appended claims the term "perfume" is used in its ordinary sense to refer to and include any non-water soluble fragrant substance or mixture of substances including natural (i.e., obtained by extraction of flower, herb, blossom or plant), artificial (i.e., mixture of natural oils or oil constituents) and synthetically produced substance) odoriferous substances. Typically, perfumes are complex mixtures of blends of various organic compounds such as alcohols, aldehydes, ethers, aromatic compounds and varying amounts of essential oils (e.g., terpenes) such as from 0% to 80%, usually from 10% to 70% by weight, the essential oils themselves being volatile odoriferous compounds and also serving to dissolve the other components of the perfume.

Suitable essential oils are selected from the group consisting of: Anethole 20/21 natural, Aniseed oil china star, Aniseed oil globe brand, Balsam (Peru), Basil oil (India), Black pepper oil, Black pepper oleoresin 40/20, Bois de Rose (Brazil) FOB, Borneol Flakes (China), Camphor oil, White, Camphor powder synthetic technical, Cananga oil (Java), Cardamom oil, Cassia oil (China), Cedarwood oil (China) BP, Cinnamon bark oil, Cinnamon leaf oil, Citronella oil, Clove bud oil, Clove leaf, Coriander (Russia), Coumarin 69° C. (China), Cyclamen Aldehyde, Diphenyl oxide, Ethyl vanilin, Eucalyptol, Eucalyptus oil, Eucalyptus citriodora, Fennel oil, Geranium oil, Ginger oil, Ginger oleoresin (India), White grapefruit oil, Guaiacwood oil, Gurjun balsam, Heliotropin, Isobornyl acetate, Isolongifolene, Juniper berry oil, L-methyl acetate, Lavender oil, Lemon oil, Lemongrass oil, Lime oil distilled, Litsea Cubeba oil, Longifolene, Menthol crystals, Methyl cedryl ketone, Methyl chavicol, Methyl salicylate, Musk ambrette, Musk ketone, Musk xylol, Nutmeg oil, Orange oil, Patchouli oil, Peppermint oil, Phenyl ethyl alcohol, Pimento berry oil, Pimento leaf oil, Rosalin, Sandalwood oil, Sandenol, Sage oil, Clary sage, Sassafras oil, Spearmint oil, Spike lavender, Tagetes, Tea tree oil, Vanilin, Vetyver oil (Java), Wintergreen, Allocimene, Arbanex™, Arbanol®, Bergamot oils, Camphene, Alpha-Campholenic aldehyde, I-Carvone, Cineoles, Citral, Citronellol Terpenes, Alpha-Citronellol, Citronellyl Acetate, Citronellyl Nitrile, Para-Cymene, Dihydroanethole, Dihydrocarveol, d-Dihydrocarvone, Dihydrolinalool, Dihydromyrcene, Dihydromyrcenol, Dihydromyrcenyl Acetate, Dihydroterpineol, Dimethyloctanal, Dimethyloctanol, Dimethyloctanyl Acetate, Estragole, Ethyl-2 Methylbutyrate, Fenchol, Fernlol™, Florilys™, Geraniol, Geranyl Acetate, Geranyl Nitrile, Glidmint™ Mint oils, Glidox™, Grapefruit oils, trans-2-Hexenal, trans-2-Hexenol, cis-3-Hexenyl Isovalerate, cis-3-Hexanyl-2-methylbutyrate, Hexyl Isovalerate, Hexyl-2-methylbutyrate, Hydroxycitronellal, Ionone, Isobornyl Methylether, Linalool, Linalool Oxide, Linalyl Acetate, Menthane Hydroperoxide, 1-Methyl Acetate, Methyl Hexyl Ether, Methyl-2-methylbutyrate, 2-Methylbutyl Isovalerate, Myrcene, Nerol, Neryl Acetate, 3-Octanol, 3-Octyl Acetate, Phenyl Ethyl-2-methylbutyrate, Petitgrain oil, cis-Pinane, Pinane Hydroperoxide, Pinanol, Pine Ester, Pine Needle oils, Pine oil, alpha-Pinene, beta-Pinene, alpha-Pinene Oxide, Plinol, Plinyl Acetate, Pseudo Ionone, Rhodinol, Rhodinyl Acetate, Spice oils, alpha-Terpinene, gamma-Terpinene, Terpinene-4-OL, Terpineol, Terpinolene, Terpinyl Acetate, Tetrahydrolinalool, Tetrahydrolinalyl Acetate, Tetrahydromyrcenol, Tetralol®, Tomato oils, Vitalizair, Zestoral™, Hinokitiol™ and Thujopsis Dolabrata™.

The disinfectant agent which can be a quaternary ammonium compound is selected from the group consisting of $C_8$–$C_{16}$ alkyl amines, $C_8$–$C_{16}$ alkyl benzyl dimethyl ammonium chlorides, $C_8$–$C_{16}$ dialkyl dimethyl ammonium chlorides, $C_8$–$C_{16}$ alkyl, $C_8$–$C_4$ alkyl dimethyl ammonium chloride and chlorohexidine and mixtures thereof. Some typical disinfectant agent useful in the instant compositions are manufactured by Lonza, S. A. They are: Bardac 2180 (or 2170) which is N-decyl-N-isonoxyl-N, N-dimethyl ammonium chloride; Bardac 22 which is didecyl dimethyl ammonium chloride; Bardac LF which is N,Ndioctyl-N, N-dimethyl ammonium chloride; Bardac 114 which is a mixture in a ratio of 1:1:1 of N-alkyl-N, N-didecyl-N, N-dimethyl ammonium chloride/N-alkyl-N, N-dimethyl-N-ethyl ammonium chloride; and Barquat MB-50 which is N-alkyl-N, N-dimethyl-N-benzyl ammonium chloride. The preferred disinfecting agent is a $C_8$–$C_{16}$ alkyl benzyl dimethyl ammonium chloride.

The cleaning compositions can optionally including at a concentration of 0 to 2.5 wt. %, more preferably 0.1 to 1.5 wt. % a proton donating agent selected from the group consisting of nonhydroxy containing organic acids such as succinic acid, glutaric acid, adipic acid, hydroxy containing organic acids such as ortho hydroxy benzoic acid, citric acid and lactic acid and inorganic acids such as sulfuric acid, hydrochloric acid and phosphoric acid and mixtures thereof.

In addition to the previously mentioned essential and optional constituents of the light duty liquid detergent, one may also employ normal and conventional adjuvants, provided they do not adversely affect the properties of the detergent. Thus, there may be used various coloring agents and perfumes; ultraviolet light absorbers such as the Uvinuls, which are products of GAF Corporation; sequestering agents such as ethylene diamine tetraacetates; magnesium sulfate heptahydrate; pearlescing agents and opacifiers; pH modifiers; etc. The proportion of such adjuvant materials, in total will normally not exceed 15% of weight of the detergent composition, and the percentages of most of such individual components will be a maximum of 5% by weight and preferably less than 2% by weight. Sodium formate can be included in the formula as a perservative at a concentration of 0.1 to 4.0%. Sodium bisulfite can be used as a color stabilizer at a concentration of 0.01 to 0.2 wt. %. Other ingredients which have been added to the compositions at concentrations of 0.1 to 4.0 wt. percent are sodium bisulfite, ETDA, isoethanoeic acid and proteins such as lexine protein.

The instant body care compositions and light duty liquid compositions can contain a polymeric thickening agent at a concentration of 0 to 3 wt. %, more preferably 0.1 wt. % to 2 wt. %. The polymeric thickening agent is selected from the group consisting of hydroxy alkyl cellulosis such as hydroxy ethyl cellulose, xanthan gums, noncrosslinked polyacrylic acids having a molecular weight of about 5,000 to about 40,000 and crosslinked polyacrylic acids having a molecular weight of about 100,000 to about 2,000,000.

The instant compositions explicitly exclude alkali metal silicates and alkali metal builders such as alkali metal polyphosphates, alkali metal carbonates, alkali metal bicarbonates, alkali metal phosphonates and alkali metal citrates because these materials, if used in the instant composition, would cause the composition to have a high pH as well as leaving residue on the surface being cleaned.

The following examples illustrate liquid cleaning compositions of the described invention. The exemplified compositions are illustrative only and do not limit the scope of the invention. Unless otherwise specified, the proportions in the examples and elsewhere in the specification are by weight.

EXAMPLE 1

The following solutions of $C_{14}$–$C_{16}$ alpha olefin sulfonates were made by adding NaOH and then $H_2O_2$ to a 30 wt. % to 40 wt. % aqueous solution of a $C_{14}$–$C_{16}$ alpha olefin having a pH of 10 to 12 and stirring the solution at a temperature of 77° F. to 150° F. for a period of 6 hours to 48 hours. Sufficient sodium hydroxide is added to the above solution to readjust the pH to about 10 to about 12. The solutions of $C_{14}$–$C_{16}$ alpha olefin sulfonate were diluted to 5 wt. % of the $C_{14}$–$C_{16}$ alpha olefin sulfonate and tested for color on a Klett-Summersen colormeter, Industrial Model 900-3.

EXAMPLE 2

The following body care compositions were made in wt. %.

| | Wt. % |
|---|---|
| C12-C14 alpha olefin sulfonate (Bleached 35.15 wt. % solution of Example 1) | 14.8 (solution) |
| Decyl polyglucoside | 2.5 |
| EDTA | 0.05 |
| Glucamate DOE-120 | 0.025 |
| Triclosan | 0.15 |
| Polyquaterum-7 | 0.05 |
| Cocoamidopropyl dimethyl betaine | 2.46 |
| Glydant | 0.4 |
| Perfume | 0.3 |
| Citric acid anhydrous | 0.1 |
| NaCl | 0.5 |
| Water | Balance |
| Appearance | Clear, colorless |
| pH | 6.0 |
| Brookfield viscosity 20 rpms, #4 spindle, RT (cps) | 5,000 |

The above sample was aged at 77° F. and 120° F. for eight weeks and the composition remained color stable at both temperatures.

EXAMPLE 3

The following light duty liquid detregent compositions were made in wt. %.

| | Wt.% |
|---|---|
| C12-C14 alpha olefin sulfonate (Bleached 35.15 wt. % solution of Example 1) | 41.00 (solution) |
| Neodol 1-9 | 14.70 |
| Cocoamidopropyl dimethyl betaine | 4.41 |
| Dodecyl polyglucoside | 4.41 |
| Laurylmyristyl monoethanolamide | 2.94 |
| Triclosan | 0.19 |
| Ethanol | 4.00 |
| Urea | 1.50 |
| Sodium xylene sulfonate | 1.18 |
| NaCl | 1.00 |
| Perfume | 0.38 |
| Citric acid anhydrous | 0.30 |
| Hydroxy ethyl EDTA | 0.12 |
| Sodium bisulfite | 0.11 |
| Dowicil 75 | 0.04 |
| Water | Balance |
| Appearance | Clear, colorless |
| pH | 5.2 |
| Brookfield viscosity 20 rpms, #21 spindle, RT (cps) | 250 |

What is claimed:

1. A body cleaning composition comprising approximately by weight:
   (a) 3% to 30% of a 30% to 40% aqueous solution of a $C_{14}$–$C_{16}$ alpha olefin sulfonate, wherein the aqueous solution has a Klett color of less than 12, when said aqueous solution is diluted to a 5% solution;
   (b) 0.1% to 8% of a $C_8$–$C_{16}$ alkyl polyglucoside;
   (c) 0.05% to 2% of a disinfecting agent;
   (d) 0.1% to 8% of a zwitterionic surfactant;
   (e) 0.05 to 2.5% of an alkali metal halide;
   (f) 0.05% to 1% of 1,3-Bis(Hydroxy methyl)-5,5-Dimethyl imidaz-olidine-2,4-dione(+); and
   (g) the balance being water.

2. The composition according to claim 1 further including a proton donating agents.

3. The composition according to claim 1 further including a disinfecting agent.

4. The composition according to claim 1 further including a polymeric thickening agent.

5. The composition according to claim 1 further including an alkali metal halide.

* * * * *